US009822056B2

(12) United States Patent
Lemaire et al.

(10) Patent No.: US 9,822,056 B2
(45) Date of Patent: Nov. 21, 2017

(54) PROCESS FOR PREPARING A CARBOXYLIC ACID

(71) Applicants: Avril, Paris (FR); Oleon SA, Compiègne (FR); Université Claude Bernard Lyon 1, Villeurbanne (FR); Centre National de la Recherche Scientifique (CNRS), Paris (FR)

(72) Inventors: Marc Lemaire, Villeurbanne (FR); Estelle Metay, Vaulx en Velin (FR); Marc Sutter, Lyons (FR); Yann Raoul, Soissons (FR); Eric Da Silva, Lyons (FR); Sophie Sambou, Fosses (FR); Philippe Blach, Margny-les-Compiegne (FR)

(73) Assignees: Avril (FR); Oleon SA (FR); Centre National de la Recherche Scientifique (CNRS) (FR); Université Claude Bernard Lyon 1 (FR)

( * ) Notice: Subject to any disclaimer, the term of this patent is extended or adjusted under 35 U.S.C. 154(b) by 0 days.

(21) Appl. No.: 15/107,855

(22) PCT Filed: Dec. 24, 2014

(86) PCT No.: PCT/FR2014/053551
§ 371 (c)(1),
(2) Date: Jun. 23, 2016

(87) PCT Pub. No.: WO2015/097418
PCT Pub. Date: Jul. 2, 2015

(65) Prior Publication Data
US 2016/0326084 A1    Nov. 10, 2016

(30) Foreign Application Priority Data

Dec. 24, 2013  (FR) .................................... 13 63565

(51) Int. Cl.
| | |
|---|---|
| *C07C 51/16* | (2006.01) |
| *C07C 51/245* | (2006.01) |
| *C07C 51/23* | (2006.01) |
| *C07C 67/333* | (2006.01) |
| *A23L 33/10* | (2016.01) |
| *A01N 37/02* | (2006.01) |
| *A61K 8/36* | (2006.01) |
| *A61K 8/362* | (2006.01) |
| *A61K 8/37* | (2006.01) |
| *B01J 21/04* | (2006.01) |
| *B01J 21/08* | (2006.01) |
| *B01J 37/08* | (2006.01) |
| *C07C 51/25* | (2006.01) |
| *C07C 51/353* | (2006.01) |
| *C07C 67/30* | (2006.01) |
| *C08K 5/09* | (2006.01) |
| *C08K 5/092* | (2006.01) |
| *C08K 5/101* | (2006.01) |
| *C08K 5/11* | (2006.01) |
| *C09J 11/06* | (2006.01) |
| *C10M 129/40* | (2006.01) |
| *C10M 129/42* | (2006.01) |

(52) U.S. Cl.
CPC ............ *C07C 51/245* (2013.01); *A01N 37/02* (2013.01); *A23L 33/10* (2016.08); *A61K 8/361* (2013.01); *A61K 8/362* (2013.01); *A61K 8/37* (2013.01); *B01J 21/04* (2013.01); *B01J 21/08* (2013.01); *B01J 37/08* (2013.01); *C07C 51/23* (2013.01); *C07C 51/25* (2013.01); *C07C 51/353* (2013.01); *C07C 67/30* (2013.01); *C07C 67/333* (2013.01); *C08K 5/09* (2013.01); *C08K 5/092* (2013.01); *C08K 5/101* (2013.01); *C08K 5/11* (2013.01); *C09J 11/06* (2013.01); *C10M 129/40* (2013.01); *C10M 129/42* (2013.01); *A23V 2002/00* (2013.01); *C10M 2207/126* (2013.01); *C10M 2207/127* (2013.01)

(58) Field of Classification Search
CPC .................................................. C07C 51/245
USPC ......................................................... 562/523
See application file for complete search history.

(56) References Cited

U.S. PATENT DOCUMENTS 4,006,173 A * 2/1977 Zeidler ................. C07C 51/235
554/136

FOREIGN PATENT DOCUMENTS

| DE | EP 2502899 A1 * | 9/2012 | ........... C07C 51/285 |
|---|---|---|---|
| EP | 2502899 A1 | 9/2012 | |

OTHER PUBLICATIONS

Kulik, A. et al : Gold-catalyzed synthesis of dicarboxylic and monocarboxylic acids, European Journal of Lipid Science and Technology , vol. 114 , No. 11, 2012, pp. 1327-1332.*
Santacesaria E et al : Double bond oxidative cleavage of monoenic fatty chains, Catalysis Today, vols. 79-80, 2003, pp. 59-65.*
E. Santacesaria, et al., "Double bond oxidative cleavage of monoenic fatty chains", Catalysis Today, vols. 79-80, Apr. 30, 2003, pp. 59-65.
Anna Kulik, et al., "Gold-catalyzed synthesis of dicarboxylic and monocarboxylic acids", European Journal of Lipid Science and Technology, vol. 114, Issue 11, pp. 1327-1332, Nov. 2012.

* cited by examiner

*Primary Examiner* — Deborah D Carr
(74) *Attorney, Agent, or Firm* — St. Onge Steward Johnston & Reens, LLC

(57) ABSTRACT

A process for preparing a carboxylic acid, including a step of bringing at least one vicinal diol or at least one vicinal polyol into contact with an atmosphere including oxygen, and a catalyst, and in the absence of additional solvent.

13 Claims, No Drawings

PROCESS FOR PREPARING A CARBOXYLIC ACID

FIELD OF THE INVENTION

The present invention relates to a process for preparing a carboxylic acid.

BACKGROUND OF THE INVENTION

The oxidative cleavage of olefins may generally take place in a single step or in two steps, either directly from olefins, or after a prior hydroxylation step of these compounds.

In general, these processes are known to be often hazardous, toxic and difficult to perform due to the presence of toxic solvents, oxidizing agents and/or catalysts, which are difficult to recycle and/or flammable and hazardous.

In neighboring technologies, the oxidative cleavage of various vicinal diols, especially of dihydroxylated stearic acid, uses a catalyst (gold) supported on alumina, in an oxidizing medium, as is described by Kockritz et al. (Eur. J. Lipid Sci. Technol. 2012, 114, 1327-1332).

Mention may also be made of processes for producing carboxylic acids from vicinal diols using $Na_2WO_4$ as catalyst (Santacesaria et al. Catalysis Today, 2003, 79-80, pages 59-65).

However, these carboxylic acid preparation processes are known to be hazardous, difficult to perform and to require the use of catalysts that are often toxic, expensive and difficult to recycle, or that require the use of one or more solvents.

There is thus a need to develop novel technologies allowing the oxidative cleavage of diols for the purpose of obtaining carboxylic acids, which are less difficult to perform, have good (high) degrees of conversion, are economically accessible and are more environmentally friendly.

SUMMARY OF THE INVENTION

The aim of the present invention is thus to develop a novel method that is easier to perform, using compounds that are more environmentally friendly and/or less expensive.

To this end, the subject of the invention is a process for preparing carboxylic acid comprising a step of placing at least one vicinal diol or at least one vicinal polyol in contact with an atmosphere comprising oxygen, a catalyst and in the absence of additional solvent, the catalyst having the formula I below:

$$[Al_nSi_mO_pM_q][A]_r \quad (I)$$ 

in which:
n, m and q are natural integers ($\mathbb{N}$), which may be identical or different, chosen, independently of each other, such that n, m and q may simultaneously be equal to 0;
p is a nonzero natural integer ($\mathbb{N}^*$);
r is zero or equal to 1;
M corresponds to at least one chemical element chosen from zirconium, tungsten, titanium and rare-earth metals, and
A corresponds to at least one chemical element chosen from alkaline-earth metals, alkali metals, rare-earth metals and titanium.

Advantageously, the invention relates to the abovementioned process, in which said catalyst is not $Na_2WO_4$.

In one of the aspects, a subject of the invention is an abovementioned process for preparing carboxylic acid, in which M is not tungsten. In other words, in this aspect, M corresponds to at least one chemical element chosen from zirconium, titanium and rare-earth metals.

Another aspect of the invention relates to an abovementioned process in which the catalyst is free of transition metals.

The process according to the invention has the advantage of not using additional solvents, which makes it possible to reduce the reaction costs, to limit the risks of pollution of the environment and/or to reduce the hazardousness of the reaction.

In addition, the process according to the invention has the advantage of not using, as cocatalyst, any metals other than those envisaged mentioned as compounds A. Generally, these other metals are expensive and difficult to recycle. Thus, the use of a catalyst of formula (I) which is sufficient in itself makes it possible to reduce the costs associated with the reaction and/or to reduce the impact on the environment.

Advantageously, the atmosphere comprising oxygen is an atmosphere enriched in oxygen or constituted of oxygen. In this atmosphere, oxygen is advantageously in the form of dioxygen.

Even more advantageously, the atmosphere containing oxygen is ambient air or is an atmosphere comprising an amount of oxygen at least equal to that present in ambient air (i.e. about 20% of the gas volume).

Typically, in this reaction, oxygen is the oxidizing agent for the reaction.

The use of oxygen in the air as oxidizing agent has the advantage of reducing the hazardousness of the reaction and of not resorting to an addition of additional oxidizing products that might be toxic to the environment.

An advantageous aspect of the invention is thus a process not using any oxidizing agent other than oxygen contained in air or a gaseous mixture of equivalent hazardousness.

The element A contained in the catalyst corresponds to a chemical element or to a group of chemical elements selected from alkaline-earth metals and alkali metals (groups 1 and 2 of the Periodic Table of the Elements).

The alkali metals are lithium, sodium, potassium, rubidium, cesium and francium.

The alkaline-earth metals are beryllium, magnesium, calcium, strontium, barium and radium.

In a nonexhaustive manner, the rare-earth metals are cerium, scandium, yttrium, lanthanum, praseodymium, neodymium, europium, promethium, samarium, europium, gadolinium, terbium, dysprosium, holmium, erbium, thulium, ytterbium and lutetium.

Advantageously, M is an element or a group of elements chosen from zirconium, tungsten, titanium, hydrogen, an element among the rare-earth metals listed above or a mixture thereof. Advantageously, A is an element or a group of elements chosen from sodium, calcium, magnesium, beryllium, potassium or a mixture thereof.

Advantageously, the catalyst of formula (I) always comprises at least one oxygen atom and may be in hydrated form, i.e. also comprising in the general formula (I) at least one water molecule.

The term "solvents" means organic compounds comprising at least one carbon atom and inorganic compounds free of carbon which have the capacity of dissolving or diluting at least one of the products used or obtained via the process of the invention.

The expression "absence of solvent" should be understood in its most common sense as not excluding the presence of a minimum amount of solvent, or "trace". Such an amount may be quantified, for example, as being less than or equal to 1% by mass of the reaction medium, preferably less than 0.1%. The reaction is preferably performed in the absence of additional solvent, i.e. without adding organic solvent or inorganic solvent, including water.

According to another advantageous aspect of the invention, the process may lead to the formation of solvent during the reaction: in such a case, the solvent obtained is not additional solvent.

According to an advantageous embodiment of the invention, the catalyst is an alumina or aluminum oxide, a silica, a zirconia, an aluminosilicate, a zeolite, an acidic clay or a mixture thereof or a mixed oxide formed from a solid solution or a mixture of solid solutions.

Aluminum oxide or alumina has the chemical formula $Al_2O_3$. It exists in the natural state and is commercially available for sale, especially from the company Sigma-Aldrich, under the reference A6139 ALDRICH.

Silica, of chemical formula $SiO_2$, is a material that is very abundant in nature in the form of quartz, and is commercially available for sale, especially from the company Sigma-Aldrich, under the reference 381276 ALDRICH.

Zirconia is a ceramic of formula $ZrO_2$ which may be obtained via standard sintering or plasma projection processes. It is also commercially available for sale from the company Sigma-Aldrich, under the reference 230693 ALDRICH.

Aluminosilicates include several materials of varied formulae, corresponding to the class of minerals containing aluminum oxide and silica oxide. For example, mention may be made of andalusite, sillimanite, kayanite, topaz or beryl. Andalusite, sillimanite and kayanite have the same composition and have the formula $Al_2O(SiO_4)$, whereas topaz has a similar chemical composition corresponding to $Al_2O(SiO_4)(OH,F)_2$. Beryl, of formula $Be_3Al_2(Si_6O_{18}$, containing $(SiO_3)_6$ rings), is also known under the name aquamarine. Hydrated aluminum silicates of the kaolinite group having the formula $Al_2Si_2O_5(OH)_4$ and generally having a three-dimensional structure in tetrahedral and/or octahedral leaflets such as dickite $Al_2Si_2O_5(OH)_4$, endelite $Al_2Si_2O_5(OH)_4.2(H_2O)$, halloysite $Al_2Si_2O_5(OH)_4$, kaolinite $Al_2Si_2O_5(OH)_4$, nacrite $Al_2Si_2O_5(OH)_4$, and odinite (Fe, Mg, Al,Fe,Ti,Mn)$_{2.5}$(Si,Al)$_2O_5$(OH)$_4$, may also be found under this name.

Zeolites are microporous minerals belonging to the group of silicates, subgroup of tectosilicates in which they form a family comprising hydrated aluminosilicates of metals, from groups 1 and 2 of the Periodic Table of the Elements (such as calcium, magnesium or potassium). Zeolites are constituted of $SiO_4$ and $AlO_4$ tetrahedra, linked together via oxygen atoms. These bonds must satisfy Loëwenstein's rule, namely that the same oxygen cannot be bonded to two aluminum atoms.

They include several materials of varied chemical formulae comprising the following common backbone, in which x1 to x9 are positive or zero integers: $Na_{x1} Ca_{x2} Mg_{x3} Ba_{x4} K_{x5} [Al_{x6} Si_{x7} O_{x8}], x9H_2O$.

These materials are thus hydrates of formula (I) according to the invention in which A corresponds to a group of elements $[Na_{x1} Ca_{x2} Mg_{x3} Ba_{x4} K_{x5}]$, x1, x2, x3, x4 and x5 being nonzero integers, and in which n=x6, m=x7, p=x8 and q=0.

Zeolites may be of natural or synthetic origin.

As nonlimiting examples of natural zeolites, mention may be made of: zeolites of the analcime family (analcime, pollucite), zeolites of the chabazite family (faujasite, chabazite, epistilbite), zeolites of the gismondine family (gonnardite), zeolites of the harmotome family (harmotone, phillipsite), zeolites of the heulandite family (heulandite, laumontite), zeolites of the natrolite family (natrolite, mesolite), zeolites of the stilbite family (barrerite, stilbite) or undetermined zeolites (tetranatolite).

As nonlimiting examples of synthetic zeolites, mention may be made of: zeolite "A" or LTA, zeolites "Y", faujasite "X", zeolite ZSM-5, mordenite or ferrierite. The processes for preparing a good number of synthetic zeolites are well known and many zeolites are commercially available for sale, for example zeolites Y (referenced CBV500, CBV712, CBV720, CBV760, CBV790) and mordenite (reference CP811G-300) are sold by the company Zeolyst International.

The mixed oxides are advantageously constituted of a simple oxide $Al_2O_3$, $TiO_2$, $SiO_2$, $ZrO_2$ and of a metal oxide $MO_x$, with M and x as described previously.

A mixture of solid solution is advantageously constituted of at least one solid solution, a solid solution being a mixture of elements at the atomic scale, similar to a mixture of liquids that are mutually soluble, for example a solidification of a liquid mixture of two pure metals A and B (or of one metal and of a nonmetallic element) whose analysis may be performed by means of a phase diagram, to obtain a binary alloy AB generally constituted in the solid state of an aggregate of one or more species of crystals. The crystals are themselves formed from mixtures of two atomic species A and B, known as solid solutions.

In yet another advantageous embodiment, the invention relates to the process described above, in which the catalyst is aluminum oxide, alone.

Thus, in an advantageous embodiment, the invention relates to a process for preparing carboxylic acid comprising a step of placing at least one vicinal diol or at least one vicinal polyol in contact with an atmosphere comprising oxygen, a catalyst and in the absence of additional solvent, the catalyst being alumina or silica, especially calcined silica.

According to another advantageous embodiment of the invention, the catalyst used is silica or zirconia.

Thus, the process according to the invention allows the preparation of carboxylic acids in a single step using aluminum oxide as catalyst, without resorting to the use of a metal also having catalytic activity, not included in element A, such as gold or ruthenium. In other words, the process according to the invention does not comprise any catalyst based on gold or ruthenium. Besides its great availability, alumina oxide is an inexpensive, nontoxic compound which can be recycled via techniques that are easy to perform, known to those skilled in the art.

The term "vicinal diol" means any compound having a carbon-based structure of varied, linear, branched or cyclic nature, bearing at least two successive hydroxyl groups, a vicinal diol being a diol in which the hydroxyl groups are borne by adjacent carbons.

The catalyst used in the process of the invention advantageously has a specific surface area of from 50 to 200 m$^2$/g, preferably from 100 m$^2$/g to 175 m$^2$/g, more preferentially 150 m$^2$/g.

According to a particular aspect of the invention, the catalyst may be in basic, neutral or acidic form, preferably in basic or acidic form respectively of formula (I) $[Al_n Si_m O_p M_q] [A]_r^-$ for the basic form and $[Al_n Si_m O_p M_q]_r^+$ for the acidic form.

The catalyst then undergoes a standard treatment for obtaining such a basic or acidic form.

According to a particular aspect of the invention, the catalyst may be in basic, neutral or acidic form, preferably in basic or acidic form respectively of formula (I) [Al$_n$ Si$_m$ O$_p$ Zr$_q$] [A]$_r^-$ for the basic form and [Al$_n$ Si$_m$ O$_p$ Zr$_q$] [A]$_r^+$ for the acidic form. According to another aspect of the invention, the catalyst may be calcined or non-calcined. The calcined catalyst results from gradual or non-gradual intense heating of the material exposed to temperatures ranging from 150 to 600° C.

The process of the invention may optionally comprise an additional prior step of hydroxylation of an unsaturated olefin making it possible to obtain the vicinal diol or the vicinal polyol required for the process according to the invention.

For example, it is possible to perform this step of hydroxylation of an unsaturated olefin in the presence of KMnO$_4$ in basic solution and water.

Advantageously, the polyol or the olefin is derived from a plant oil.

The olefin used in the context of the invention is a fatty acid or a fatty acid ester bearing a carbon-based chain of 10 to 30 carbon atoms, preferably from 12 to 20 carbon atoms, typically 12, 13, 14, 15, 16, 17, 18, 19 or 20 carbon atoms.

Preferably, the fatty acid ester bears an alkyl group of 1 to 5 carbon atoms: advantageously, the group is a methyl.

The olefin may also be substituted with one or more alkyl and/or hydroxyl groups, the alkyl group ranging from 1 to 5 carbon atoms and is advantageously a methyl.

The fatty acid or the fatty acid ester described in the invention is advantageously chosen from the group constituted by myristoleic acid, palmitoleic acid, oleic acid, ricinoleic acid, gadoleic acid, erucic acid, nervonic acid, linoleic acid, α-linolenic acid, γ-linolenic acid, di-homo-γ-linolenic acid, arachidonic acid, timnodonic acid and cervonic acid, and derivatives thereof.

According to a particularly advantageous embodiment of the invention, the vicinal diol is methyl 9,10-dihydroxystearate.

According to an advantageous embodiment of the invention, the mole ratio between oxygen or dioxygen and said at least one vicinal diol or at least one vicinal polyol is from 0.6 to 3.5 equivalents, preferably from 1 to 2 equivalents and even more preferentially 1.5 equivalents.

Advantageously, the reaction taking place during the step of placing in contact of the various compounds according to the process of the invention is an oxidative cleavage reaction. It makes it possible to obtain at least one, and preferentially two, identical or different compounds such as carboxylic acids.

The term "carboxylic acid" means any compound having a structure of varied linear, branched or cyclic nature, bearing at least one carboxylic acid function.

Advantageously, the carboxylic acid obtained is a mono- or dicarboxylic acid, or a mixture thereof, i.e. a carboxylic acid comprising, respectively, one or two carboxylic acid functions.

The carboxylic acids may be substituted with one or more alkyl groups and/or hydroxyl groups. They may also advantageously bear at least one ester function, the alkyl group of which bears from 1 to 5 carbon atoms, advantageously is a methyl.

Advantageously, such carboxylic acids have a carbon-based chain ranging from 2 to 28 carbon atoms, preferably from 4 to 24 carbon atoms, typically 8, 9, 10, 11, 12, 13, 14, 15, 16, 17, 18, 19, 20, 21 or 22 carbon atoms. The advantageous carboxylic acids are hexanoic (caproic) heptanoic, octanoic (caprylic), nonanoic (pelargonic), decanoic (capric), undecanoic, 1,6-hexanedioic (adipic), 1,7-heptanedioic, 1,8-octanedioic, 1,9-nonanedioic (azelaic), 1,10-decanedioic (sebacic), 1,11-undecanedioic, 1,12-dodecanedioic, 1,13-tridecanedioic (brassylic), 1,14-tetradecanedioic and 1,15-pentadecanedioic acids.

Even more advantageously, in the case where the vicinal diol used is methyl 9,10-dihydroxystearate, the products obtained are pelargonic acid and azelaic acid, alone or as a mixture.

The catalyst is advantageously used in an amount corresponding to from 0.1% to 10% by weight of the mixture (mass percentage), preferably from 1% to 10% and more preferably from 5% to 10% by weight of the mixture.

The reaction is advantageously performed at a temperature from 60 to 200° C., more particularly 90 to 150° C.

The reaction is advantageously performed at a pressure from 1 to 40 bar. Even more advantageously, the pressure is from 30 to 40 bar. Preferably, the reaction pressure is 31, 32, 33, 34, 35, 36, 37, 38 or 39 bar.

Advantageously, the reaction is performed with stirring. The process according to the invention may take place in a reactor with magnetic stirring or with mechanical stirring. Typically, the reactor used is one with mechanical stirring.

The process according to the invention may be performed using a starting material with a degree of purity ranging from 65% to percentages above 99% by weight of the composition. Preferably, the starting material has a purity of greater than 95%, and even more advantageously the purity is greater than 99% by weight of the composition.

The invention also relates to the use of a catalyst in solid form having the formula I below:

$$[Al_nSi_mO_pM_q][A]_r \qquad (I)$$

in which:

n, m and q are natural integers ℕ, which may be identical or different, chosen, independently of each other, such that n=m=q is other than zero;

p is a nonzero natural integer ℕ*;

r is zero or equal to 1;

M corresponds to at least one chemical element chosen from zirconium, tungsten, titanium and rare-earth metals, and A corresponds to at least one chemical element chosen from alkaline-earth metals, alkali metals, rare-earth metals and titanium, for performing a process for producing carboxylic acids from vicinal diol or polyol, said process not involving any addition of solvent.

The invention also relates to the use of alumina or silica as catalyst for performing a process for producing carboxylic acids from vicinal diol or polyol as defined previously.

Advantageously, the invention relates to the use of alumina as catalyst for performing a process for producing carboxylic acids from vicinal diol or from vicinal polyol, especially from methyl 9,10-dihydroxystearate for the synthesis of pelargonic acid and azelaic acid.

The invention also relates to a composition comprising, essentially comprising or consisting of a mixture of pelargonic acid, or a derivative thereof, and of azelaic acid, or a derivative thereof, said mixture comprising a pelargonic acid/azelaic acid ratio ranging from 40:60 to 70:30.

The abovementioned composition may be obtained via the process as defined previously, and also in the examples that follow.

The abovementioned composition may also comprise up to 50% of 9,10-dihydroxystearic acid. In other words, the composition comprises, essentially comprises or consists of a mixture
of pelargonic acid, and/or a derivative thereof,
of azelaic acid, and/or a derivative thereof, and
of 9,10-dihydroxystearic acid, and/or a derivative thereof,
the composition being such that it comprises up to 50% by weight of the composition of 9,10-dihydroxystearic acid relative to the total weight of the composition, and said mixture comprises a pelargonic acid/azelaic acid ratio ranging from 40:60 to 70:30.

This means that if the composition comprises 50% 9,10-dihydroxystearic acid, it comprises 50% of a mixture of pelargonic acid and of azelaic acid, this mixture comprising from 20% to 35% by weight of pelargonic acid relative to the total weight of the composition, and from 15% to 35% by weight of azelaic acid relative to the total weight of the composition.

The term "acid or a derivative thereof" means in the invention the salts of said acid, or its ionic forms, or alternatively an ester, especially a methyl ester, of the acid function.

Thus, in the invention:
a pelargonic acid derivative may be a sodium, potassium, etc. pelargonate or a methyl pelargonate,
an azelaic acid derivative may be a sodium, potassium, etc. azelate or a methyl or dimethyl azelate, and
a 9,10-dihydroxystearic acid derivative may be a sodium, potassium, etc. 9,10-dihydroxystearate or a methyl 9,10-dihydroxystearate.

The invention also relates to the use of the abovementioned composition for the preparation of biolubricants and/or low-temperature plasticizers and/or adhesives and/or products for the food or cosmetics industry, and/or in the context of protecting crops. The composition may be used in unmodified form, or after purification of its main components, i.e. azelaic acid and pelargonic acid.

For the term "use in the context of protecting crops", examples that may be mentioned include use of the composition as a herbicide in order to combat herbaceous or ligneous weeds or any other plant that competes with cultivated plants. This herbicidal action may be total or partial depending on the desired effect.

Azelaic acid may be used in a wide range of applications: biolubricants, low-temperature plasticizers, adhesives, food, cosmetic and pharmaceutical industries.

The uses of pelargonic acid are also varied: as an ingredient in lubricants, alkyd resins and plasticizers, but also more commonly in protecting crops, as far as into niche markets such as the treatment of surfaces or substrates or alternatively in controlled release systems.

DETAILED DESCRIPTION OF THE INVENTION

The invention will be understood more clearly on reading the examples, which do not have any limiting nature.

EXAMPLES

Example 1: Preparation of an Alumina or Silica Catalyst According to the Invention: Example of Calcined Catalyst Alumina or silica (20 g), in powder form, is calcined for 3 hours up to 550° C., with a temperature increase of the order of 2° C. per minute. The calcined alumina or silica is then stored in a desiccator so as to protect it from moisture.

Example 2: Process for Esterifying and Purifying Methyl 9,10-Dihydroxystearate The starting methyl 9,10-dihydroxystearate has a purity ranging from 60%-70%.

An amount of 30 g of methyl 9,10-dihydroxystearate, i.e. 90 mM, is placed in contact with 400 mL of pentane. The mixture is stirred for 2 hours at room temperature.

The solvent is then removed by filtration and the precipitate is dried under vacuum. 25 g of a precipitate are recovered, i.e. 83% by weight of the mixture.

The products obtained on conclusion of the reaction (oxidation products) are esterified for the purposes of the analysis techniques.

To this end, the precipitate is placed in contact with methanol (200 mL) and Amberlyst 15 (10% by weight) and refluxed overnight at 80° C.

The resin thus obtained is removed by filtration and the filtrate is evaporated under vacuum.

The precipitate is finally recrystallized from hot in the methanol.

17 g of 9,10DHSM are obtained (57% yield) in a purity of greater than 98% (analysis by NMR and GC).

Example 3: Reactivity of Methyl 9,10-Dihydroxystearate in Oxidizing Medium in the Absence of Catalyst: Control An amount of 9.5 g (equivalent to 28.8 mmol) of methyl 9,10-dihydroxystearate is placed in a 300 mL autoclave with mechanical stirring.

The reaction is performed at 140° C. for 15 hours under 8 bar of air according to the following reaction scheme:

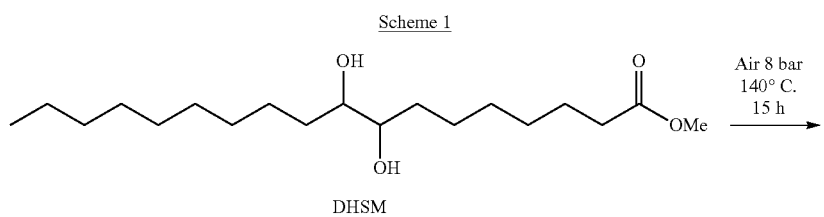

Scheme 1

DHSM

-continued

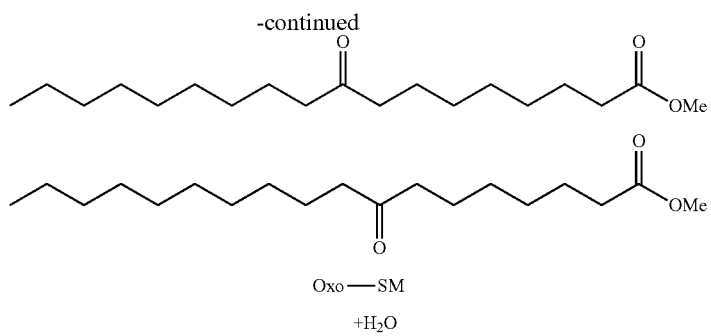

Oxo—SM

+H₂O

After cooling to room temperature, an orange oil is obtained corresponding to 95% by weight of the initial mixture.

The reaction medium is analyzed by gas chromatography after dissolution in methanol.

A mixture of methyl 9 and/or 10-oxostearate is obtained after identification by mass spectrometry and proton and carbon nuclear magnetic resonance.

In the absence of catalyst, no oxidative cleavage is observed, but transformation (rearrangement) of the diol into ketone is observed: this is an isophysical reaction without any change in the degree of oxidation.

Example 4: Oxidative Cleavage of Methyl 9,10-Dihydroxystearate According to the Process of the Invention The oxidative cleavage reaction of the process according to the invention was performed, according to the following reaction scheme, under various conditions of amount of substrate, of calcined or non-calcined catalyst and of reaction times:

a) In the presence of calcined basic alumina: 2 g of DHSM a1) Oxidative cleavage An amount of 2 g (equivalent to 6.06 mmol) of methyl 9,10-dihydroxystearate (DHSM) is placed in a 300 mL autoclave with magnetic stirring, in the presence of calcined alumina oxide (i.e. 5% by weight of the mixture). The mixture is maintained at 140° C. for 16 hours under 8 bar of air (mole $O_2$=20 mmol), the reaction takes place according to step 1) of the above reaction scheme.

The mixture is cooled to room temperature, and an orange oil is obtained (corresponding to 90% by weight of the mixture).

a2) Esterification

The products obtained on conclusion of the reaction (oxidation products) are esterified for the purposes of the analysis techniques.

To this end, the reaction medium is diluted in 50 mL of methanol and is then filtered, step 2) of the above reaction scheme. Next, 10% by weight of Amberlyst® is added to the filtrate, which is refluxed for 5 hours.

The resin is removed by filtration and the filtrate is then evaporated under reduced pressure.

Scheme 2

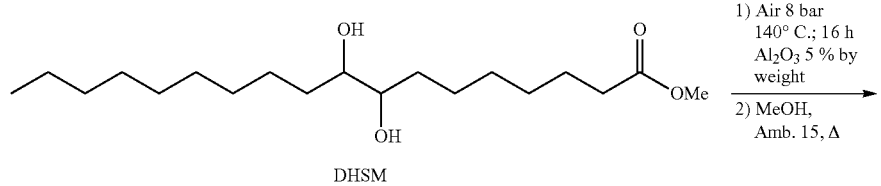

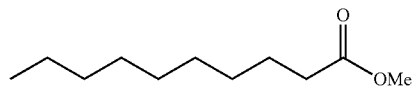

Pelargonic acid (PA)

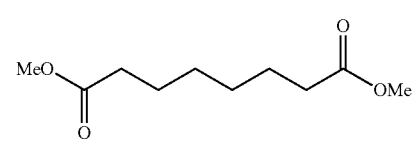

Azelaic acid (AA)

The crude product is analyzed by gas chromatography and by NMR.

A mixture of methyl pelargonate (PM) and dimethyl azelate (ADM) is obtained with a PM/ADM ratio of 64/36.

The DHSM conversion is 100%.

b) In the presence of calcined basic alumina: 12 g of DHSM b1) Oxidative cleavage An amount of 12 g (equivalent to 36.4 mmol) of methyl 9,10-dihydroxystearate is placed in a 300 mL autoclave with mechanical stirring, in the presence of calcined alumina oxide (5% by weight).

The mixture is maintained at 140° C. for 16 hours under 8 bar of air (mole $O_2$=20 mmol), the reaction takes place according to step 1) of the above reaction scheme.

The mixture thus obtained is cooled to room temperature, and an orange oil is obtained (corresponding to 90% by weight of the mixture).

b2) Esterification

The products obtained on conclusion of the reaction (oxidation products) are esterified for the purposes of the analysis techniques.

To this end, the reaction medium is diluted in 50 mL of methanol and is then filtered, step 2) of the preceding reaction scheme. Next, 10% by weight of Amberlyst® is added to the filtrate, which is refluxed for 5 hours.

The resin is removed by filtration and the filtrate is then evaporated under reduced pressure.

The crude product is analyzed by gas chromatography and by NMR.

A mixture of methyl pelargonate (PM) and of dimethyl azelate (ADM) is obtained with a PM/ADM ratio of 65/35.

The DHSM conversion is 64%.

c2) In the presence of non-calcined basic alumina—24 h c1) Oxidative cleavage

An amount of 2 g (equivalent to 6.06 mmol) of methyl 9,10-dihydroxystearate is placed in a 300 mL autoclave with magnetic stirring, in the presence of non-calcined alumina oxide (5% by weight). The mixture is maintained at 140° C. for 24 hours under 8 bar of air (mole $O_2$=20 mmol), the reaction takes place according to step 1) of the above reaction scheme.

The mixture thus obtained is cooled to room temperature, and an orange oil is obtained (93% by weight).

c2) Esterification

The products obtained on conclusion of the reaction (oxidation products) are esterified for the purposes of the analysis techniques.

To this end, the reaction medium is diluted in 50 mL of methanol and is then filtered (step 2) of the preceding reaction process). Next, 10% by weight of Amberlyst® is added to the filtrate, which is refluxed for 5 hours.

The resin is removed by filtration and the filtrate is then evaporated under reduced pressure.

The crude product is analyzed by gas chromatography and by NMR.

A mixture of methyl pelargonate (PM) and of dimethyl azelate (ADM) is obtained with a PM/ADM ratio of 63/37.

The DHSM conversion is 100%.

d) In the presence of calcined basic alumina—5 h d1) Oxidative cleavage

An amount of 2 g (equivalent to 6.06 mmol) of methyl 9,10-dihydroxystearate is placed in a 300 mL autoclave with magnetic stirring, in the presence of calcined alumina oxide (5% by weight).

The mixture is maintained at 140° C. for 5 hours under 8 bar of air (mole $O_2$=20 mmol), and the reaction takes place according to step 1) of the above reaction scheme.

The mixture thus obtained is cooled to room temperature, and an orange oil is obtained (92% by weight).

d2) Esterification

The products obtained on conclusion of the reaction (oxidation products) are esterified for the purposes of the analysis techniques.

To this end, the reaction medium is diluted in 50 mL of methanol and is then filtered (step 2) of the preceding reaction scheme). Next, 10% by weight of Amberlyst® is added to the filtrate, which is refluxed for 5 hours.

The resin is removed by filtration and the filtrate is then evaporated under reduced pressure.

The crude product is analyzed by gas chromatography and by NMR.

A mixture of methyl pelargonate (PM) and of dimethyl azelate (ADM) is obtained with a PM/ADM ratio of 50/50.

The DHSM conversion is 100%.

e) In the presence of non-calcined neutral alumina—5 h e1) Oxidative cleavage

An amount of 2 g (equivalent to 6.06 mmol) of methyl 9,10-dihydroxystearate is placed in a 300 mL autoclave with mechanical stirring, in the presence of non-calcined neutral alumina oxide (5% by weight).

The mixture is maintained at 140° C. for 5 hours under 8 bar of air (mole $O_2$=20 mmol), and the reaction takes place according to step 1) of the above reaction scheme.

The mixture thus obtained is cooled to room temperature, and an orange oil is obtained (corresponding to 90% by weight of the mixture).

e2) Esterification

The products obtained on conclusion of the reaction (oxidation products) are esterified for the purposes of the analysis techniques.

To this end, the reaction medium is diluted in 50 mL of methanol and is then filtered (step 2) of the preceding reaction scheme). Next, 10% by weight of Amberlyst® is added to the filtrate, which is refluxed for 5 hours.

The resin is removed by filtration and the filtrate is then evaporated under reduced pressure.

The crude product is analyzed by gas chromatography and by NMR.

A mixture of methyl pelargonate (PM) and of dimethyl azelate (ADM) is obtained with a PM/ADM ratio of 65/35.

The DHSM conversion is 64%.

f) In the presence of calcined basic alumina—5 h f1) Oxidative cleavage

An amount of 15 g (equivalent to 45.5 mmol) of methyl 9,10-dihydroxystearate is placed in a 300 mL autoclave with magnetic stirring, in the presence of calcined alumina oxide (5% by weight).

The mixture is maintained at 140° C. for 5 hours under 30 bar of air (mole $O_2$=20 mmol), and the reaction takes place according to step 1) of the above reaction scheme.

The mixture thus obtained is cooled to room temperature, and an orange oil is obtained (corresponding to 88% by weight of the mixture).

f2) Esterification

The products obtained on conclusion of the reaction (oxidation products) are esterified for the purposes of the analysis techniques.

To this end, the reaction medium is diluted in 50 mL of methanol and is then filtered, step 2) of the preceding reaction scheme. Next, 10% by weight of Amberlyst® is added to the filtrate, which is refluxed for 5 hours.

The resin is removed by filtration and the filtrate is then evaporated under reduced pressure.

The crude product is analyzed by gas chromatography and by NMR.

A mixture of methyl pelargonate (PM) and of dimethyl azelate (ADM) is obtained with a PM/ADM ratio of 65/35.

The DHSM conversion is 60%.

The isolated yield after distillation is 23% and 21% for methyl pelargonate and dimethyl azelate, respectively.

g) In the presence of calcined silica g1) Oxidative cleavage

An amount of 15 g (equivalent to 45.5 mmol) of methyl 9,10-dihydroxystearate (DHSM) with a purity of about 97% is placed in a 300 mL autoclave with mechanical stirring, in the presence of calcined silica (5% by weight).

The mixture is maintained at 140° C. for 5 hours under 30 bar of air (68 mmol of O2), and the reaction takes place according to step 1 (described previously).

The mixture thus obtained is cooled to room temperature, and an orange oil is obtained (corresponding to 89% by weight of the mixture).

g2) Esterification

The products obtained on conclusion of the reaction (oxidation products) are then 100% esterified for the purposes of the analysis techniques. To this end, the reaction medium is diluted in 300 mL of methanol and is then filtered, step 2) of the preceding reaction scheme. Next, 10% by weight of Amberlyst® are added to the filtrate, which is refluxed for 16 hours. The resin is removed by filtration and the filtrate is then evaporated under reduced pressure. An orange oil is obtained (corresponding to 88% by weight of the mixture).

The crude reaction product is analyzed by gas chromatography and by proton NMR. The inventors obtained a mixture of methyl pelargonate (PM) and of dimethyl azelate (ADM) with a PM/ADM ratio of 46/54.

The DHSM conversion is greater than 95%.

The summary of the results obtained is given in the table below:

TABLE 1

| Ex No. | Cat. | Time (H) | Ratio $O_2$/DHSM | Conv. (%) DHSM | Ratio (%) PM/ADM | Sel. (%) C9/C8 |
|---|---|---|---|---|---|---|
| a | Calcined basic $Al_2O_3$ | 16 | 3.3 | 100 | 64/36 | 84/16 |
| b | Calcined basic $Al_2O_3$ | 16 | 0.6 | 64 | 65/35 | 80/20 |
| c | Non-calcined basic $Al_2O_3$ | 24 | 3.3 | 100 | 63/37 | 83/17 |
| d | Calcined basic $Al_2O_3$ | 5 | 3.3 | 100 | 50/50 | 95/5 |
| e | Non-calcined neutral $Al_2O_3$ | 5 | 3.3 | 100 | 65/35 | 97/3 |
| f | Calcined basic $Al_2O_3$ | 5 | 1.5 | 60 | 45/55 | 95/5 |
| g | Calcined silica | 5 | 1.5 | >95 | 46/54 | 97/3 |

Example 5: Preparation of a Silica Catalyst According to the Invention: Example of a Calcined Catalyst Silica (5 g), in powder form, is calcined for 3 hours up to 550° C., with a temperature increment of about 2° C. per minute. The calcined silica is then stored in a desiccator in order to protect it from moisture.

Example 6: Oxidative Cleavage of 9,10-Dihydroxystearic Acid According to the Process of the Invention—Catalysis with Alumina or Silica The 9,10-dihydroxystearic acid (DHSA) has a purity of 80.8%.

The oxidative cleavage reaction of the process according to the invention was performed, according to the following reaction scheme, in the presence of various natures of calcined substrate:

Scheme 3

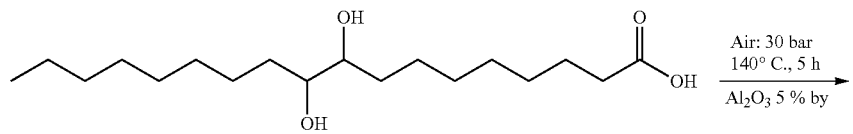

DHSM

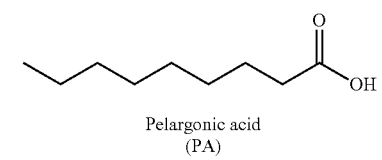

Pelargonic acid (PA)

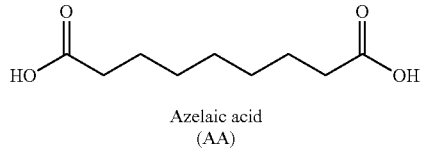

Azelaic acid (AA)

a) In the presence of calcined basic alumina:

An amount of 60 g (equivalent to 153 mmol) of 9,10-dihydroxystearic acid (DHSA) is placed in a 600 mL autoclave with magnetic stirring, in the presence of calcined basic alumina oxide (i.e. 5% by weight of the mixture; prepared under the conditions of example 1). The mixture is maintained at 140° C. for 5 hours under 30 bar of air (mole $O_2$=107 mmol), and the reaction takes place according to the above reaction scheme.

The mixture is cooled to room temperature, and an orange oil is obtained (corresponding to 90% by weight of the mixture).

The crude product is analyzed after esterification by gas chromatography. A mixture of methyl pelargonate (PM) and of dimethyl azelate (ADM) is obtained with a PM/ADM ratio of 15/85. The DHSA conversion is 94%.

b) In the presence of calcined neutral alumina:

An amount of 60 g (equivalent to 153 mmol) of 9,10-dihydroxystearic acid (DHSA) is placed in a 600 mL autoclave with magnetic stirring, in the presence of calcined neutral alumina oxide (i.e. 5% by weight of the mixture; prepared under the conditions of example 1). The mixture is maintained at 140° C. for 5 hours under 30 bar of air (mole $O_2$=524 mmol), and the reaction takes place according to the above reaction scheme.

The mixture is cooled to room temperature, and an orange oil is obtained (corresponding to 90% by weight of the mixture).

The crude product is analyzed after esterification by gas chromatography. A mixture of methyl pelargonate (PM) and of dimethyl azelate (ADM) is obtained with a PM/ADM ratio of 55/45. The DHSA conversion is 90%.

c) In the presence of calcined silica:

An amount of 60 g (equivalent to 153 mmol) of 9,10-dihydroxystearic acid (DHSA) is placed in a 600 mL autoclave with magnetic stirring, in the presence of calcined silica (i.e. 5% by weight of the mixture; prepared under the conditions of example 1). The mixture is maintained at 140° C. for 5 hours under 30 bar of air (mole $O_2$=524 mmol), and the reaction proceeds according to the above reaction scheme.

The mixture is cooled to room temperature, and an orange oil is obtained (corresponding to 90% by weight of the mixture).

The crude product is analyzed after esterification by gas chromatography. A mixture of methyl pelargonate (PM) and of dimethyl azelate (ADM) is obtained with a PM/ADM ratio of 35/65. The DHSA conversion is 86%.

The invention claimed is:

1. A process for preparing carboxylic acid comprising a step of placing at least one vicinal diol or at least one vicinal polyol in contact with an atmosphere comprising oxygen, a catalyst and in the absence of additional solvent, the catalyst having the formula I below:

$$[Al_nSi_mO_pM_q][A]_r \qquad (I)$$

wherein:
n, m and q are natural integers (ℕ), which may be identical or different, chosen, independently of each other, such that n, m and q may simultaneously be equal to 0;
p is a nonzero natural integer (ℕ*);
r is zero or 1;
M corresponds to at least one chemical element chosen from zirconium, tungsten, titanium and rare-earth metals, and
A corresponds to at least one chemical element chosen from alkaline-earth metals, alkali metals, rare-earth metals and titanium;
wherein the catalyst is one of the following catalysts: $Al_2O_3$, $SiO_2$, $TiO_2$, and $ZrO_2$.

2. The process according to claim 1, wherein the catalyst has a specific surface area of from 50 to 200 $m^2/g$.

3. The process according to claim 1, comprising a prior step of hydroxylation of an olefin or of hydrolysis of an epoxide.

4. The process according to claim 1, wherein the at least vicinal diol or the at least vicinal polyol is derived from a plant oil.

5. The process according to claim 3, wherein the olefin is a fatty acid or a fatty acid ester bearing a carbon-based chain of 10 to 30 carbon atoms.

6. The process according to claim 5, wherein the fatty acid or the fatty acid ester is chosen from the group consisting of myristoleic acid, palmitoleic acid, oleic acid, ricinoleic acid, gadoleic acid, erucic acid, nervonic acid, linoleic acid, α-linolenic acid, γ-linolenic acid, di-homo-γ-linolenic acid, arachidonic acid, timnodonic acid, and cervonic acid.

7. The process according to claim 1, wherein the at least vicinal diol is methyl 9,10-dihydroxystearate.

8. The process according to claim 1, wherein the carboxylic acid is a monocarboxylic acid or a dicarboxylic acid, or a mixture thereof.

9. The process according to claim 1, wherein the carboxylic acid obtained from the process is a mixture of pelargonic acid and azelaic acid.

10. The process according to claim 1, wherein the reaction step is performed at a pressure from 1 to 40 bar.

11. The process according to claim 1, wherein a mole ratio between dioxygen and said at least one vicinal diol or said at least one vicinal polyol is from 0.6 to 3.5 equivalents.

12. The process according to claim 2, wherein the catalyst has a specific surface area of 150 $m^2/g$.

13. The process according to claim 3, wherein the olefin is derived from a plant oil.

* * * * *